United States Patent
Akula

(10) Patent No.: US 9,522,598 B2
(45) Date of Patent: Dec. 20, 2016

(54) VEHICLE OCCUPANT EMERGENCY SYSTEM

(71) Applicant: Verizon Patent and Licensing Inc., Arlington, VA (US)

(72) Inventor: Sneha Akula, Atlanta, GA (US)

(73) Assignee: VERIZON PATENT AND LICENSING INC., Basking Ridge, NJ (US)

(*) Notice: Subject to any disclaimer, the term of this patent is extended or adjusted under 35 U.S.C. 154(b) by 0 days.

(21) Appl. No.: 14/688,452

(22) Filed: Apr. 16, 2015

(65) Prior Publication Data

US 2016/0303969 A1 Oct. 20, 2016

(51) Int. Cl.
*B60K 35/00* (2006.01)
*G01C 21/34* (2006.01)
*G05D 1/00* (2006.01)
*A61B 5/00* (2006.01)

(52) U.S. Cl.
CPC ............... *B60K 35/00* (2013.01); *A61B 5/486* (2013.01); *A61B 5/6893* (2013.01); *A61B 5/7282* (2013.01); *A61B 5/747* (2013.01); *A61B 5/7475* (2013.01); *G01C 21/3407* (2013.01); *G05D 1/0088* (2013.01); *B60K 2350/1004* (2013.01)

(58) Field of Classification Search
CPC ....... B60K 35/00; A61B 5/486; A61B 5/6893; A61B 5/7282; A61B 5/747; A61B 5/7475; G01C 21/3407; G05D 1/0088
See application file for complete search history.

(56) References Cited

U.S. PATENT DOCUMENTS

| | | | | |
|---|---|---|---|---|
| 6,166,627 A * | 12/2000 | Reeley | ............... | B60R 25/102 340/426.18 |
| 6,897,788 B2 * | 5/2005 | Khair | ............... | A61B 5/0006 128/903 |
| 7,431,120 B2 * | 10/2008 | Pollehn | ............ | B60H 1/00742 180/272 |
| 8,874,301 B1 * | 10/2014 | Rao | ................. | B60K 28/066 180/272 |
| 2006/0251293 A1 * | 11/2006 | Piirainen | ............ | B60N 2/002 382/104 |
| 2010/0168527 A1 * | 7/2010 | Zumo | ............... | A61B 5/0205 600/301 |
| 2012/0256769 A1 * | 10/2012 | Satpathy | ......... | G08B 13/19647 340/989 |
| 2013/0226369 A1 * | 8/2013 | Yorio | ................ | G06F 17/00 701/1 |
| 2013/0231582 A1 * | 9/2013 | Prasad | ............... | A61B 5/746 600/551 |
| 2014/0310594 A1 * | 10/2014 | Ricci | ................. | H04W 48/04 715/702 |

* cited by examiner

*Primary Examiner* — Calvin Cheung

(57) ABSTRACT

A system may include a user interface, a transmitter, a processor, and a memory having a program communicatively connected to the processor. The processor may be configured to receive a body sensor output associated with an occupant of a vehicle, receive a vehicle sensor output associated with the vehicle, compare the body and vehicle sensor outputs with a threshold, prompt for a confirmation associated with at least one of the body and vehicle sensor outputs, determine an issue type based on at least one of the body and vehicle sensor outputs, and send a notification including the issue type.

17 Claims, 4 Drawing Sheets

VEHICLE OCCUPANT EMERGENCY SYSTEM

BACKGROUND

Traditional vehicles, such as autonomous vehicles, may include sensors focused on an external environment of the vehicle, for example, to operate the vehicle along a road while avoiding obstacles. Traditional vehicles may also include sensors focused on an internal environment of the vehicle, such as an air temperature inside the vehicle, but these sensors have no ability to measure and detect medical issues associated with body parameters, such as a body temperature, of occupants in the vehicle. Consequently, traditional vehicles lack the ability to respond to medical issues of one or more occupants of the vehicle. Further, these traditional vehicles lack the ability to communicate medical issues with nearby vehicles as well as emergency vehicles, facilities, and call centers. Additionally, typical vehicles lack the ability to automatically communicate with and route occupants to facilities that are capable of treating the medical issues. Accordingly, there is a need for a system configured to detect, communicate, and respond to medical issues, e.g., using one or more sensors associated with the body parameters of one or more occupants of the vehicle.

DETAILED DESCRIPTION

A system may include a user interface, a transceiver, a processor, and a memory having a program communicatively connected to the processor. The processor may be configured to receive a body sensor output associated with an occupant of a vehicle, receive a vehicle sensor output associated with the vehicle, compare the body and vehicle sensor outputs with a threshold, prompt for a confirmation associated with at least one of the body and vehicle sensor outputs, determine an issue type based on at least one of the body and vehicle sensor outputs, and send a notification including the issue type.

The processor may further be configured to receive a facility list having a medical capability and a facility location for a plurality of facilities, select one of the plurality of facilities from the facility list based in part on a comparison between the medical issue and the medical capability of at least a portion of the plurality of facilities, and determine a route to the selected facility. The processor may further be configured to instruct a vehicle computer of the vehicle to drive the vehicle to the selected facility based on the determined route.

Figure 1:
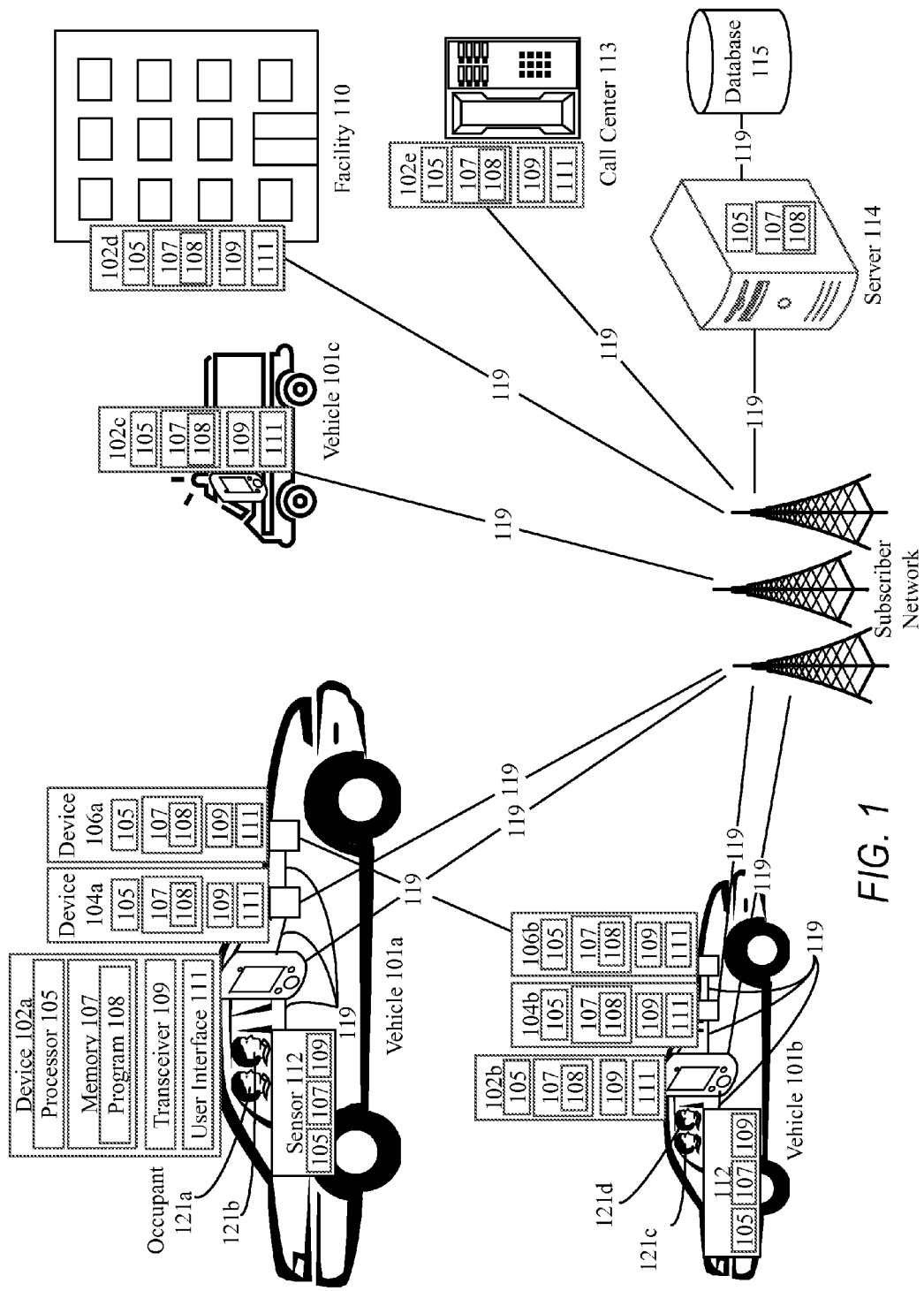
FIG. 1 illustrates an exemplary system of the present disclosure.

FIG. 1 illustrates an exemplary system 100, for example, to communicate occupant information. System 100 may take many different forms and include multiple and/or alternate components and facilities. While an exemplary system 100 is shown in FIG. 1, the exemplary components illustrated in FIG. 1 are not intended to be limiting. Indeed, additional or alternative components and/or implementations may be used.

As illustrated in FIG. 1, system 100 may include a vehicle 101 (e.g., vehicles 101a-c), a device 102 (e.g., devices 102a-d), a device 104 (e.g., devices 104a-b), a device 106 (e.g., devices 106a-b), a facility 110, a sensor 112, a call center 113, a server 114, a database 115, a subscriber network 117, and communication links or connections 119. The system 100 may be configured to be utilized by a vehicle occupant 121 (e.g., occupants 121a-d). The devices 102, 104, and 106, sensor 112, and server 114 may include a processor 105 and a memory 107. A program 108 may be loaded to the memory 107 and may include instructions to be executed by the processor 105. The devices 102, 104, and 106 and sensor 112 may include a transceiver 109 or separate transmitters and receivers in place of a transceiver 109. The devices 102, 104, and 106 may include a user interface 111.

The occupant information may include any information or data associated with one or more occupants 121 or vehicle 101. The occupant information may be received using the user interface 111, stored as part of memory 107 or database 115, communicated between any of devices 102, 104, and 106, sensor 112, and server 114 using transceiver 109, and displayed as part of the user interface 111. The occupant information may include sensor outputs including one or more issues including, for example, one or more medical issues associated with one or more occupants 121 of vehicle 101, one or more vehicle issues associated with vehicles 101, or a combination issue including one or more medical issues and one or more vehicle issues, as discussed in further detail below. The occupant information may further include location information such as an occupant location or vehicle location provided by devices 102 and 104, as also discussed in more detail below. The occupant information may include medical records of one or more occupants 121, which may be stored as part of memory 107 or database 115. The occupant information may further include an occupant history reflecting prior medical issues, vehicle collisions, vehicle citations (e.g., speeding or parking tickets), and criminal offenses (e.g., operating while intoxicated or other alcohol related offenses), which may be stored as part of memory 107 or database 115. Thus, the occupant information transferred between and utilized by any of devices 102, 104, and 106, sensor 112, server 114, and database 115.

The system 100 may include an overall network infrastructure through which the devices 102, 104, and 106, sensor 112, server 114, and database 115 may communicate, for example, to transfer occupant information between any of devices 102, 104, and 106, sensor 112, server 114, and database 115, e.g., using connections 119. For instance, the system 100 may generally include edge, distribution, and core devices (e.g., server 114) and enables a path (e.g., connection 119) for the exchange of occupant information between different devices and systems (e.g., between any of devices 102, 104, and 106, sensor 112, server 114, and database 115). In general, a network (e.g., system 100 or subscriber network 117) may be a collection of computing devices and other hardware to provide connections and carry communications.

Further, the system 100 may utilize any networking technology including, for example, any wired or wireless network. The network may include a packet network or any other network having an infrastructure to carry communications. Exemplary networks may include one or more of a cellular network, a vehicle-to-vehicle (V2V) communication network, telephone network, global area network, wide area networks (WAN), a VoIP network, an LTE network, a VoLTE (Voice over LTE) network, fiber optic network, cable network, television network, local area networks (e.g., Ethernet), wireless local area networks (e.g., radio-frequency (RF) or Wi-Fi), power-line networks, private networks (e.g., configured to provide network access limited to devices having network-specific software), or combinations thereof. The system 100 is provided as an example, and thus while a system 100 is illustrated, this illustration may represent a single network infrastructure, a combination of different networks components and technologies, and/or a plurality of networks.

Subscriber network 117 may be configured to provide communications services to and between a plurality of devices (e.g., devices 102, 104, and 106 and server 114). The subscriber network 117 may provide communications services, such as packet-switched network services (e.g., Internet access, VoIP (Voice over Internet Protocol) communication services) and location services (e.g., device positioning), to devices connected to the subscriber network 117. Exemplary subscriber network 117 may include any network discussed above, for example a cellular network, a telephone network, VoIP network, an LTE network, a VoLTE (Voice over LTE) network, a fiber optic network, or any combination thereof. Subscriber network 117 may also be configured to generate occupant information including an occupant location, for example a current geographic position of any of devices 102 or 104.

The vehicle 101 may include any vehicle such as any land, air, or water vehicle. Exemplary vehicles 101*a-b* may include any passenger or transit vehicle. Further, an exemplary vehicle 101*c* may include an emergency vehicle such as an ambulatory, police, firefighting, or roadside assistance vehicle. The vehicle 101 may be configured to be selectively controlled by the device 106 with varying levels of driver input including human input, for example, by occupant 121. An exemplary occupant 121 may include any person occupying the vehicle 101 such as driver or passenger. Exemplary human inputs may include, for example, steering with a steering wheel, acceleration with an accelerator pedal, and braking with a brake pedal of the vehicle 101. For example, the human inputs may be provided by the occupant 121 to direct the vehicle 101 along a route, for example, to the facility 110.

The sensor 112 may include any sensor configured to measure and monitor occupant information and generate one or a plurality of sensor outputs associated with one or more occupants 121 or vehicle 101. The sensor 112 may also be configured to detect occurrence of and generate sensor outputs indicating one or more issues including, for example, a medical issue such as a body disorder associated with one or more occupants 121, a vehicle issue such as a malfunction, damage, or accident associated with the vehicle 101, or a combination issue including medical and vehicle issues. The sensor 112 may be configured to communicate, using the transceiver 109, the sensor outputs indicating the issue to devices 102, 104, and 106 in communication with other devices 102, 104, and 106 and server 114.

The sensor 112 may include a body sensor configured to detect and generate one or more body sensor outputs in response to a medical issue associated with one or more occupants 121. The sensor 112 may be configured to measure one or more body parameters associated with one or more occupants 121. The sensor 112 may include any wired or wireless sensor, for example, any health monitor or any wearable, contact, or non-contact sensor. The sensor 112 may be unattached, releasably attached, or permanently attached with respect to the occupant 121 or vehicle 101. An exemplary sensor 112 may include a heart rate monitor, cardiac sensor, blood glucose meter, respirometer, spirometer, respiration sensor, optical sensor, electrocardiogram (EKG), medical imaging device, medical radar device, pulse oximeter, blood pressure monitor, body temperature monitor, breathalyzer, chemical sensor, or moisture sensor. The sensor outputs may include body parameters such as a heart rate, glucose level, respiratory rate, eye response, oxygen saturation, blood pressure, body temperature, blood alcohol content, presence of blood, or a combination thereof. The sensor 112, using transceiver 109, may be configured to communicate one or more sensor outputs (e.g., real-time, near real-time, periodically, or upon occurrence of the medical issue) to the devices 102 and 104, which may communicate occupant information along with the sensor output to other devices 102 and 104, devices 106, and server 114.

The sensor 112 may further include a vehicle sensor configured to detect and generate one or more vehicle sensor outputs in response to a vehicle issue associated with the vehicle 101, for example, apart from or in combination with a medical issue of occupant 121. An exemplary sensor 112 may include, for example, a vehicle condition sensor such as tire pressure sensor, engine sensor, glass break sensor, or crash sensor. An exemplary sensor 112 may also include a vehicle environment sensor such as a motion detector, microphone, or camera that are positioned inside, outside, or otherwise associated with the vehicle 101. For example, the sensor 112 may be configured to detect motion of the occupant 121, noise or speech from the occupant 121, or a visual image of the occupant 121. The sensor 112, using transceiver 109, may be configured to communicate a sensor output (e.g., real-time, near real-time, periodically, or upon occurrence of the vehicle issue) to the devices 102, 104, and 106 and server 114.

A threshold associated with the sensor outputs may be stored as part of memory 107 or database 115. The threshold may be utilized by the device 102 to determine whether a possible issue is present in the occupant 121, vehicle 101, or a combination thereof. The threshold may be predefined (e.g., by occupant 121) as part of the memory 107 or database 115 and may include a threshold number, a threshold sequence, a lower threshold, an upper threshold, or a threshold range having lower and upper thresholds. The threshold number may be satisfied by a predetermined number of sensor outputs, e.g., two or more sensor outputs may satisfy the threshold. Further, the threshold sequence may be satisfied with a vehicle sensor output and a body sensor output occurring in a predefined order, within a predefined time period of each other, or a combination thereof. In addition, the threshold range may be satisfied if the sensor outputs are below the lower threshold, above the upper threshold, or otherwise outside the threshold range. For example, sensor outputs beyond the predefined number of sensor outputs, above the lower threshold, below the upper threshold, or in the threshold range may indicate that an issue is present with respect to the occupant 121 or vehicle 101. Each of the medical and vehicle issues may each have a respective threshold.

For example, the threshold range for a body parameter such as a respiratory rate may have a lower threshold (e.g., approximately 10-15 breaths per minute) and an upper threshold (e.g., approximately 20-25 breaths per minute). If the sensor output indicates a respiration rate outside the threshold range, a medical issue may be present. If the sensor output indicates that the respiration rate is in the threshold range, a medical issue is not present with respect to this body parameter. If all of the parameters of the sensor outputs are in their respective threshold ranges, the device 102 may determine that no medical issue is present.

As another example, the threshold range for a body parameter such as a heart rate may have a lower threshold (e.g., approximately 20-40 beats per minute) and an upper threshold (e.g., approximately 180-200 beats per minute). If the sensor output indicates a heart rate outside the threshold range, a medical issue may be present. If the sensor output indicates that the heart rate is in the threshold range, a medical issue is not present with respect to this body parameter. If all of the parameters of the sensor outputs are in their respective threshold ranges, the device 102 may determine that no medical issue is present.

As a further example, the threshold number of sensor outputs may be satisfied when a predefined number of sensor outputs is reached, e.g., one, two, three, or more sensor outputs. The sensors 112 may include a first sensor 112 configured to generate a first sensor output, a second sensor 112 configured to generate a second sensor output, and a third sensor 112 configured to generate a third sensor output. If the predefined number of sensor outputs is two or more, the threshold number would be satisfied by any two the first, second, and third sensor outputs, but not by only one of the first, second, and third sensor outputs. Thus, a decision tree may be appropriate in the case of reviewing sensor outputs from a plurality of sensors 112 that is more sophisticated than solely relying on a threshold of a single sensor 112. As a result, satisfaction of the threshold may involve the consideration of multiple sensor outputs, whether from a single sensor 112 over time or a plurality of sensors 112.

The threshold sequence may be satisfied based on a vehicle sensor output and a body sensor output occurring in a predefined order, within a predefined time period of each other, or a combination thereof. The predefined time period may be any number of seconds or minutes. For example, the threshold sequence may be satisfied by a vehicle sensor output (e.g., indicating a vehicle crash) followed by and within a predefined time period of a body sensor output (e.g., indicating an injury resulting from the crash). Alternatively, the threshold sequence may also be satisfied by a body sensor output (e.g., indicating a medical issue) followed by and within a predefined time period of a vehicle sensor output (e.g., indicating a resulting crash).

A comparison of the sensor outputs of two or more sensors 112 may be used to determine an issue type including a medical issue, a vehicle issue, or a combination issue including both. A first sensor 112 (e.g., a body sensor) may be configured to generate a first sensor output and a second sensor 112 (e.g., a vehicle sensor) may be configured to generate a second sensor output. In response to the first sensor output, the device 102 may determine that the issue type includes a medical issue. In response to the second sensor output, the device 102 may determine that the issue type includes a vehicle issue. In response to both the first and second sensor outputs, the device 102 may determine that the issue type includes a combination issue. Similar to the threshold, a decision tree may be appropriate in the case of reviewing sensor outputs from a plurality of sensors 112 that is more sophisticated than solely relying on a threshold of a single sensor 112. As a result, determination of the issue type may involve the consideration of multiple sensor outputs, whether from a single sensor 112 over time or a plurality of sensors 112.

For example, the sensors 112 may include a moisture sensor configured to provide a sensor output in response to moisture, a chemical sensor configured to provide a sensor output in response to blood, and a crash sensor configured to provide a sensor output in response the vehicle 101 impacting another object. In response to blood contacting a moisture sensor and a chemical sensor, the moisture and chemical sensors may generate a sensor output indicating a medical issue but no vehicle issue. In response to a beverage contacting the moisture sensor, only the moisture sensor may generate a sensor output indicating no medical or vehicle issue. In response to the vehicle 101 being driven into water, both the moisture sensor and crash sensor may generate a sensor output indicating a vehicle issue but no medical issues. Accordingly, two or more sensors 112 may be utilized to determine the issue type.

The device 102 may include a computing device such as an occupant device. The device 102 may be configured to communicate information, e.g., occupant information, with devices 104, device 106, sensor 112, server 114, or other devices 102. An exemplary device 102 may include a mobile device, cellular phone, smart-phone, super-phone, tablet computer, next generation portable device, handheld computer, notebook, or laptop.

For example, the device 102*a* may receive (e.g., using the user interface 111) occupant information from one or more occupants 121, communicate (e.g., using the transceiver 109) the occupant information to any of devices 102*b-e* and server 114, receive (e.g., using the transceiver 109) a response from any of devices 102*b-e* and server 114, and display (e.g., using the user interface 111) the response to the occupant 121.

The device 104 may include a computing device such as a telematics device. The device 104 may be configured to communicate information, e.g., occupant information, with other portions of the system 100, e.g., devices 102 and other devices 104. The telematics device may be configured to provide telematics services, for example, using location information (e.g., using a global positioning system (GPS)) and the subscriber network 117 (e.g., using the transceiver 109). Exemplary telematics services may include automatic driving assistance, vehicle tracking, container tracking, cold storage tracking, fleet management, safety information (e.g., road hazard or weather notifications), emergency warning information (e.g., emergency vehicle notifications), and vehicle status (e.g., a notification of vehicle information or vehicle issues). The device 104 may be configured to access the subscriber network 117 using the transceiver 109 or by connecting with the device 102 in communication with the subscriber network 117.

The device 106 may include a computing device such as a vehicle computer. The device 106 may be configured to selectively control operation of the vehicle 101 according to one or more driving modes. Exemplary driving modes may include a driver operated mode (e.g., operation of the vehicle 101 determined by human input), a partial or semi-autonomous mode including automated, driver assistance or correction (e.g., partial operation of the vehicle 101 by device 106 along with human input), or an autonomous or driverless mode (e.g., full operation of the vehicle 101 by device 106 without human input). In the driver operated mode, the device 106 may allow human input to operate the vehicle 101 and without controlling a route of the vehicle 101. In the automated mode, the device 106 may provide automated control of the vehicle 101 (e.g., electronic stability control, automatic braking, adaptive cruise control, or lane keeping) in conjunction with human input. The autonomous driving mode may provide control of the vehicle 101 without human input or intervention, for example, guiding the vehicle 101 along a route while controlling the steering, acceleration, and braking.

The device 106, e.g., using the processor 105, may be configured to transfer driver inputs of occupant 121 with respect to vehicle controls of vehicle 101, e.g., between the occupant 121 and device 106 and between various body portions of the occupant 121. Exemplary vehicle controls may include acceleration, braking, clutch operation, and steering controls. For example, the occupant 121 may have a medical issue resulting in inhibited use of one or more first body portions (e.g., arms, hands, legs, or feet) and may wish to transfer vehicle operation to one or more second body portions (e.g., the other of arms, hands, legs, or feet). The device 102 or 104, e.g., using the user interface 111, may receive a confirmation (e.g., a verbal, textual, or tactile indication) from the occupant 121 that the medical issue is present. The device 102 or 104, e.g., using the transceiver 109, may instruct the device 106 to utilize, e.g., the partial or semi-autonomous mode. The device 106, e.g., using the partial or semi-autonomous mode, may then automatically operate one or more first vehicle controls (e.g., acceleration, braking, or clutch operation control) of the vehicle 101 while still allowing the occupant 121 to operate one or more second vehicle controls (e.g., steering control or other controls typically operated by the inhibited body portions). Alternatively, instead of the vehicle 101 taking over the first vehicle controls, the device 106 may transfer control of the first vehicle controls to the occupant 121 using an alternative control mechanism, e.g., a hand-operated control mechanism such as steering wheel paddle shifters or a turn-signal or directional stalk, configured replace the vehicle operations traditionally performed by another control mechanism. For example, the hand-operated control mechanism may be utilized to provide acceleration, braking, or clutch operation control, thereby replacing a foot-operated control mechanism. Alternatively, the device 106, e.g., using the partial or semi-autonomous mode, may change the vehicle operations that are operated by a particular control mechanism. For example, the device 106 may convert a turn-signal or directional signal stalk into an acceleration control. The device 102, 104, or 106, using the processor 105, may determine what level of partial, or full, autonomous control to implement on the vehicle 101, e.g., based on the confirmation from occupant 121. The device 106, e.g., using the partial autonomous mode, may be configured to transfer vehicle control between a first control mechanism (e.g., hand-operated controls) and a second control mechanism (e.g., foot-operated controls), which may be specifically adapted for such transferred control of the vehicle 101 between various body portions of the occupant 121. Thus, device 106 may be configured to transfer vehicle controls between the occupant 121 and device 106 and, in addition, between various body portions of the occupant 121.

The device 106, e.g., using the processor 105, may be configured to provide adaptive correction of the driver inputs of the occupant 121 of vehicle 101, e.g., relative to a baseline profile. The device 106 may provide adaptive correction to correct or adjust a driver input, e.g., in response to a medial issue. The device 106 may be configured to monitor, e.g., using the sensors 112, and store, e.g., as part of memory 107, the driver inputs for vehicle controls (e.g., acceleration, braking, clutch operation, and steering control) and sensor outputs over a setup time period. The device 106 may be configured to generate, e.g., using the processor 105, and store, e.g., using the memory 107, the baseline profile including, e.g., average ranges for the driver inputs and sensor outputs. With the baseline profile, the device 106, e.g., using the processor 105, may be configured to monitor the driver inputs and sensor outputs for a monitoring time interval. The device 106, e.g., using the processor 105, may be configured to then compare the driver inputs to the baseline profile and compare the sensor outputs to the baseline profile or to the threshold, as discussed above. If at least one of the driver inputs and sensor outputs are within the baseline profile (e.g., a sharp driver input such as acceleration, braking, clutch operation, or steering outside the baseline profile, but an indication that no medial or vehicle issue is present), the device 106 may continue to monitor the driver inputs for another monitoring interval. However, if the driver inputs and sensor outputs are outside the baseline profile (e.g., a sharp driver input and an indication of a medial or vehicle issue), the device 106 may notify the occupant 121 that the driver inputs and sensor outputs are outside the baseline profile (e.g., using an audio, textual, or tactile notification or a combination thereof), prompt the occupant 121 to confirm or override adaptive correction as discussed in more detail below, and implement adaptive correction thereby adjusting the driver inputs in conformance with the baseline profile. Thus, the device 106 continue to monitor the driver inputs and sensor outputs in response to only a sharp driver input, but device 106 may utilize adaptive correction in response to a sharp driver input along with a medical or vehicle issue. Alternatively, even if the driver inputs are within the baseline profile, the device 106 may apply adaptive correction in response to a medial or vehicle issue meeting the threshold.

The device 106, e.g. using adaptive correction, may adjust an input-output ratio between one or more driver inputs and a response of the vehicle 101. The device 106, e.g., using the processor 105, may increase or decrease a response by the vehicle 101 to the driver inputs, an amount of force from the occupant 121 that is required to operate the vehicle, or an amount of force from the vehicle 101 that is translated back to the occupant 121. For example, the device 106, e.g., using the processor 105, may be configured to adjust the input ratio for steering (e.g., by amplifying or dampening a vibration or steering resistance translated to the occupant 121 or a steering response of the vehicle 101) or for acceleration (e.g., by amplifying or dampening a throttle response of the vehicle 101 by adjusting a fuel injector duty cycle mapping). Further, the device 106, e.g., using the processor 105, may transfer vehicle controls and utilize the partial or semi-autonomous mode as discussed above, e.g., to adjust the vehicle controls to keep the vehicle 101 within a particular lane or operate the vehicle 101 to a side or other safe portion of a roadway. Alternatively, the device 106, e.g., using the processor 105, may utilize the autonomous mode to operate the vehicle to the facility 110, as discussed in further detail below.

The processor 105 of devices 102 and 104 and server 114 may be configured to determine without human intervention a route between an occupant location and a facility location or, in the event the vehicle 101 is inoperable due to a vehicle issue, a route may be determined between an emergency vehicle location and an occupant location. The occupant location of occupant 121 or vehicle 101a and the emergency vehicle location of vehicle 101c may be determined, for example, using the GPS of device 102 or 104. The facility location may be determined by accessing a facility list as part of memory 107 or database 115 or an internet facility directory. The route may be determined, using the processor 105, with one or more maps as part of memory 107, database 115, or an internet map directory.

In use, the device 102 or 104 may determine the occupant location using the GPS, access the facility list, select a facility 110 based on the occupant location and facility list using the processor 105 of any of devices 102 and 104 or server 114, determine the route to the facility using the processor 105 of any of devices 102 and 104 or server 114, provide the determined route to the device 106 using the transceiver 109, and direct or operate the vehicle 101 to the facility 110 using the device 106. Alternatively, the processor 105 of device 106 may determine the route and, in addition, direct or operate the vehicle 101 to the facility 110. The devices 102 and 104 may further communicate a notification including the occupant information (e.g., occupant location and the medical or vehicle condition) to the other devices 102, 104, and 106 and server 114 using the transceiver 109.

The processor 105 may further be configured to determine the route based in part on a medical severity, stored as part of memory 107 or database 115. The medical severity may be associated with one or more occupants 121 or vehicles 101. The medical severity may be assigned by the processor 105 based in part on the particular medical issues and a number of occupants 121 affected by medical issues. For example, a first medical issue associated with a life threatening condition (e.g., a major injury or body disorder such as an organ failure) may be assigned a higher medical severity and a second medical issue associated with a non-life threatening condition (e.g., a minor injury or body disorder such as a bone fracture) may be assigned a lower medical severity. Furthermore, an first occupant 121 or vehicle 101 with a higher number of medical issues (e.g., multiple injuries or body disorders) may be assigned a higher medical severity and an second occupant 121 or vehicle 101 with a lower number of medical issues (e.g., a single injury or body disorder) may be assigned a lower medical severity. Thus, the devices 102, 104, and 106, sensor 112, and server 114 may determine the route based in part on the medical severity.

The devices 102 and 104 and server 114 may be configured to selectively authorize the device 106 to utilize the automated and autonomous driving modes, for example, based on each of the automated and autonomous driving mode being permitted by applicable laws, e.g., stored as part of memory 107 or database 115, according to the occupant location or in response to a medical issue associated with one or more occupants 121. For example, the device 106 may be configured to utilize each of the automated and autonomous driving modes only when permitted by applicable laws. Alternatively, in response to a medical issue, the device 106 may utilize the autonomous driving mode even when prohibited by applicable laws, because the occupant 121 may be unable to safely drive the vehicle 101. Further, in response to a medical issue, devices 102 and 104 and server 114 may authorize the device 106 to alternatingly flash the right and left headlights, right and left taillights, and emergency warning lights (e.g., light emitting diodes (LEDs)), and blow the horn of the vehicle 101a.

The vehicle 101 may include traffic preemption devices that may be used in conjunction with the devices 102, 104, and 106 and server 114. The devices 102 and 104 may authorize the device 106 to utilize the traffic preemption devices to cause traffic lights along the route of the vehicle 101 to cycle thereby granting right-of-way along the route of the vehicle 101. More specifically, the devices 102, 104, and 106 may communicate with directly with nearby traffic lights or with server 114, which may be in communication with a computer (e.g., operated by a department of transportation) that controls the traffic lights. In response to a medical or vehicle issue, the devices 102, 104, and 106 may communicate with the traffic lights or server 114 to change the traffic signals from green to red along the route of vehicle 101. The traffic lights may change in response to the vehicle location determined using GPS, e.g., changing from red to green when the vehicle 101 approaches the traffic signals and returning to normal operation after the vehicle 101 passes the traffic signals.

The devices 102, 104, and 106 may further include a computing device such as a vehicle-to-vehicle (V2V) device, for example between devices 106a-106b. The V2V device may be configured to provide vehicle-to-vehicle (V2V) communication, for example, utilizing any vehicle-to-vehicle (V2V) communication protocol such as a dedicated short-range communications (DSRC) protocol. The V2V device, using the transceiver 109, may be configured to wirelessly exchange of vehicle data between nearby vehicles, for example, between vehicle 101a and 101b. The vehicle data may include a position, a speed, and a location of a vehicle 101, which may be determined using a global positioning system (GPS). The vehicle data may also indicate that the vehicle 101 is operating in a driver operation, automated, or autonomous driving mode. The V2V device (e.g., of vehicle 101a) may be configured to communicate with one or more other V2V devices (e.g., of vehicle 101b) to provide a notification upon or associated with entering an intersection, departing a highway, an obstacle, a sudden halt, an accident, a lane change, or nearby ambulances, fire trucks, or police cars. Thus, the devices 102, 104, and 106, using V2V communication, may communicate with nearby vehicles 101.

The devices 102, 104, and 106, sensor 112, and server 114 may be configured to communicate, using the transceiver 109, a notification including occupant information between any of devices 102, 104, and 106, sensor 112, and server 114. Exemplary notifications may include, for example, an automated phone call, short message service (SMS) or text message, e-mail, http link, web-based portal, V2V communication, or any other type of electronic communication. The notification may include occupant information, may be communicated between any of devices 102, 104, and 106 and server 114 and may be displayed as part of the user interface 111 of any of devices 102. The notification may be provided to an emergency contact list of the occupant 121, which may be stored as part of memory 107 or database 115. The notification may include a description of medical and vehicle issues. For example, the notification may additionally incorporate by way of example an automated phone call to a user such as medical, police, firefighting, ambulance, or roadside assistance personnel or another occupant 121.

In response to a medical or vehicle issue, the devices 102, 104, and 106, using the transceiver 109, may be configured to seek help from other nearby devices 102, 104, and 106. The devices 102, 104, and 106 may provide an occupant location to the server 114 and, in response, the server 114 may send a notification to other devices 102, 104, and 106 having location information nearby the occupant location. The notification may include a message seeking help along with the medical or vehicle issue. For example, the notification may be received by nearby medical professionals (e.g., doctors or nurses) using the other devices 102, 104, and 106 that may provide aid or protection.

The devices 102 and 104 may be configured to access a facility list. The facility list may include a list of facilities 110 based on the location information of device 102 or device 104. The facility list may be stored as part of memory 107 or database 115. The facility list may include a facility location and a capability level associated with each facility 110. The facility list may be generated or populated by the occupant 121, facility 110, or call center 113 using the user interface 111 of device 102 or using an internet directory accessed using the subscriber network 117 in communication with the device 102. The capability level may include a trauma center level associated with medical specialists and equipment available at each facility 110, for example, to treat medical issues associated with occupants 121. The device 102 or 104 may be configured to determine (e.g., using the GPS) an occupant location, access (e.g., using the transceiver 109) a facility list based on the occupant location, select (e.g., using the processor 105) a facility 110 from the facility list based on the occupant location and the medical issue, generate (e.g., using the processor) a route to selected facility 110, and provide the route to occupant 121 or device 106, which may drive the vehicle 101 to the selected facility 110.

The facility 110 may include any healthcare facility or other situation appropriate (e.g., safe) location for occupants 121. An exemplary facility 110 may include any facility that offers medical services including, for example, a hospital, a doctor's office, a nurse-led clinic, a health clinic, an inpatient care center, an outpatient care center, a surgical center, an ambulatory center, an urgent care center, a community health center, a retail clinic, or a free clinic.

The call center 113 may include any call center responsible for a call to an emergency telephone number for emergency services. An exemplary call center 113 may include a public-safety answering point (PSAP). Exemplary emergency services may include police, firefighting, and ambulance services. The call center 113 may also dispatch emergency services in response to the call for emergency services. The call center 113 may be configured to determine location information associated with the call by using the subscriber network 117. The call center 113 may be configured to send a notification (e.g., an automated phone call) to one or a plurality of devices 102 to provide an alert in response to the medical or vehicle issue. For example, the call center 113, using the device 102e, may receive a notification from the device 102a indicating a medical or vehicle issue and, in response, send a notification to devices 102b-d.

The server 114 may include any computing system, for example, a telematics server. The server 114 may be configured to communicatively connect with and transfer occupant information between the devices 102, 104, and 106 and database 115. The server 114 may be connected, via connection 119, to the devices 102, 104, and 106 and database 115. Server 114 may be in continuous or periodic communication with devices 102, 104, and 106. Server 114 may include a local, remote, or cloud-based server or a combination thereof and may be in communication with and provide occupant information (e.g., as part of memory 107 or database 115) to any of devices 102, 104, and 106. The server 114 may further provide a web-based user interface (e.g., an internet portal) to be displayed by any of the user interface 111 of devices 104. The server 114 may communicate the occupant information with devices 102 and 104 using a notification including, for example automated phone call, short message service (SMS) or text message, e-mail, http link, web-based portal, or any other type of electronic communication. In addition, the server 114 may be configured to store occupant information as part of memory 107 or database 115. The server 114 may include a single or a plurality of centrally or geographically distributed servers 114. Server 114 may be configured to store and coordinate occupant information with devices 102, 104, and 106 and database 115.

The devices 102, 104, and 106 may be configured to receive and respond to the sensor output of the sensor 112. The device 102, 104, and 106, using the transceiver 109, may receive the sensor output from sensor 112, e.g., including an indication of an issue such as a vehicle issue, medical issue, or a combination thereof. In response a sensor output indicating an issue or after a user-defined time period specified with user interface 111, the devices 102, 104, and 106 may prompt the occupant 121 for a confirmation including an indication associated with, for example, if the occupant 121 can safely operate the vehicle 101, if the occupant needs medical attention, if the vehicle 101 is operable, or any similar or alternative prompts. The prompt and corresponding confirmation may be indicated, for example, using any audio, verbal, visual, textual, or tactile indication, button press, sensor output, or a combination thereof. An exemplary confirmation may indicate a "yes" or "no" or any other positive or negative indication. The confirmation may also be received by the sensor 112, for example, using a button as part of the sensor 112. Thus, devices 102, 104, and 106 may be configured to determine the condition of the occupants 121 and vehicle 101.

The devices 102, 104, and 106 may be configured to respond to a confirmation or lack of confirmation from the occupant 121. If the confirmation or lack of confirmation indicates that the occupant 121 should not be driving or needs medical attention, the device 102a or 104a may select a facility 110 from the facility list based on the location information and the confirmation, instruct the device 106a to drive the vehicle 101 to the selected facility 110 (e.g., using the autonomous driving mode), and communicate a notification including occupant information to the devices 102b-e and server 114. If the confirmation or lack of confirmation indicates that the vehicle is not operable, the devices 102a-102b may send a notification to the other devices 102a-104b and server 114, which may communicate the occupant information (e.g., location information and a medical or vehicle condition) with the vehicle 101c (e.g., an emergency vehicle). Alternatively, if the confirmation indicates that the occupant 121 is okay to drive or does not need medical attention, the device 102a or 104a may instruct the vehicle 106a continue the current driving mode.

The sensor 112, devices 102 and 104, and server 114 may be configured to populate and maintain a sensor record, as part of the memory 107 or database 115. The sensor record may include the sensor outputs from sensor 112 and the associated confirmation, as discussed above. The sensor record may also include a sensor accuracy based on a number of false positives between the sensor outputs for a particular sensor 112 and the confirmation of the occupant 121. For example, if a sensor output indicates that the occupant 121 has an unreadable or an abnormally low or high body parameter while the confirmation indicates that the occupant 121 is okay, this indicates a false positive. Accordingly, a higher number of false positives results in a lower sensor accuracy as part of the sensor record of memory 107 or database 115. Alternatively, a lower number of false positives results in a higher sensor accuracy as part of the sensor record of memory 107 or database 115. Thus, the devices 102 and 104 and server 114 may utilize the sensor record to determine the sensor accuracy associated with each sensor 112.

The processor 105 may be configured to selectively implement the driver operation, automated, and autonomous driving modes, for example, as selected by the occupant 121 with user interface 111 or according to instructions from the program 108. The occupant 121 may utilize the user interface 111 to select between the driver operation, automated, and autonomous driving modes. The occupant 121 may determine this selection, for example, based on whether the occupant 121 can safely operate the vehicle 101, which may be indicated to the occupant 121 by displaying the sensor outputs indicating a medical or vehicle issue as part of user interface 111. Further, in response to a medical issue, the occupant 121 may utilize the user interface 111 to continue with or select between the driver operation, automated, and autonomous driving modes. Alternatively, in response to a medical issue, the processor 105 may automatically switch from the driver operation or automated mode to the autonomous driving mode. Further, if the vehicle 101 is not operable, the transceiver 109 of device 102a may send the occupant location to the other devices 102, which may route the vehicle 101c (e.g., an ambulatory vehicle) to the vehicle 101a.

The devices 102 and 104 and server 114 may be configured to send occupant information to the device 102c of vehicle 101c, device 102d of facility 110, and device 102e of call center 113. For example, after selecting the facility 110 as discussed above, the occupant information (e.g., medical issues and medical records) may be sent to the selected facility 110 using the transceiver 109 of the devices 102 and 104 or server 114. Further, one or more facilities 110, using the transceiver 109 of device 102d, may send occupant information (e.g., medical records for each of occupants 121) to the vehicle 101c. The server 114 or device 102d, using the processor 105, may coordinate the arrival of occupants 121 at the selected facility 110 and their respective occupant information (e.g., medical records) and present, using the user interface 111, the occupant information to medical personnel of the vehicle 101c (e.g., while traveling toward or upon arrival at vehicle 101a) or the selected facility 110 (e.g., upon arrival or during check-in). The medical personnel may review the occupant information, which may include sensor outputs and medical records. For example, the device 102d may be configured to provide a diagnosis of one or more occupants 121 remotely based on the sensor outputs and medical records, e.g., while the vehicle is in route to the facility 110. Based on the occupant information, the device 102d may be configured to expedite check-in of the occupant 121 at facility 110, route the occupant 121 to an area of the facility 110 associated with a medical issue of the occupant 121, and facilitate the preparation of equipment at the facility 110 associated with the medical issue.

Furthermore, the devices 102 and 104 and server 114 may be configured to apply a medical severity to a plurality of vehicles 101 (e.g., vehicles 101a and 101b) or occupants 121 (e.g., occupants 121a-d). For instance, an accident may involve a plurality of vehicles 101 and occupants 121. The processor 105 may evaluate the occupant information (e.g., the sensor outputs and medical records) from each of the occupants 121. The processor 105 may triage or prioritize the occupants 121 based on the medical severity, compare the medical severity and the medical capability of each facility 110, and select a facility from a facility list based on the comparison and the occupant location. For example, each facility 110 (e.g., a hospital) may be configured to, or have the capability to, accommodate a predefined number of patients, which may, or may not be, an absolute maximum. Thus, the server 114 may route one or more vehicles 101 to the facility 110 having a closer facility location to the occupant location until the facility reaches the predefined number of patients it can accommodate. After the predefined number is met, the server 114 may route vehicles to the facility 110 having the next closest facility location to the occupant location. Further, the vehicles 101 with occupants 121 having a higher medical severity may be routed to a facility 110 having the closer facility location or having a higher medical capability, even if the vehicle 101 has occupants 121 with a lower medical severity. Other vehicles 101 with occupants 121 having a lower medical severity may be routed to a facility 110 having a further facility location or a lower medical capability.

The user interface 111 of devices 102, 104, and 106 may include a display or a mechanism to connect to a display, support user interfaces, and/or communicate occupant information within the system 100. The user interface 111 may include any input or output device to facilitate the receipt or presentation of information (e.g., occupant information) in audio, visual or tactile form or a combination thereof. Examples of a display may include, without limitation, a touchscreen, a vehicle dashboard, cathode ray tube display, light-emitting diode display, electroluminescent display, electronic paper, plasma display panel, liquid crystal display, high-performance addressing display, thin-film transistor display, organic light-emitting diode display, surface-conduction electron-emitter display, laser TV, carbon nanotubes, quantum dot display, interferometric modulator display, and the like. The display may present user interfaces to any user of devices 102, 104, and 106, for example, one or more occupants 121 or any medical, police, firefighting, ambulance, or roadside assistance personnel.

The transceiver 109 (e.g., of devices 102, 104, and 106 and sensor 112) may communicatively connect the devices of system 100, for example, using any type of wired or wireless network connection. The transceiver 109 may include a single transceiver or a combination of transmitters and receivers. The wireless network may utilize a wireless transmitter (e.g., cellular, radiofrequency (RF) or Wi-Fi transmitter) of transceiver 109. Transceiver 109 may be configured to communicatively connect any or all of devices 102, 104, and 106, sensor 112, and server 114. Transceiver 109 may be used for digital or analog signal transfers. For instance, transceiver 109 may include any antenna technology including cellular, V2V communication, radiofrequency (RF), near field communication (NFC), Bluetooth®, Wi-Fi, or the like. Transceiver 109 may include any technology that implements a wireless exchange of occupant information by converting propagating electromagnetic waves to and from conducted electrical signals. Transceiver 109 may include any technology that is used to exchange occupant information wirelessly using radio waves over a radio range or network that enables communication.

The devices 102, 104, and 106 may include a location determination technology that enables the determination of location information (e.g., a current geographic position) of any of devices 102, 104, and 106. Examples of location determination technology may include, without limitation, global positioning systems (GPS), indoor positioning system, local positioning system, and mobile phone tracking. The devices 102, 104, and 106 may be configured to provide a current geographic position of any of devices 102, 104, and 106, for example, to provide an occupant location of occupant 121, a vehicle location of vehicle 101, or a facility location of facility 110.

The connections 119 may be any wired or wireless connections between two or more endpoints (e.g., devices or systems), for example, to facilitate transfer of occupant information (e.g., including subscriber information and occupant information). Connection 119 may include a wireless connection, for example, to communicatively connect the devices 102, 104, and 106 with subscriber network 117. Connection 119 may include a V2V connection, for example, to communicatively connect device 106*a* with device 106*b*. Connection 119 may include a wide area network connection, for example, to communicatively connect server 114 with subscriber network 117. Connection 119 may include a radiofrequency (RF), near field communication (NFC), Bluetooth®, Wi-Fi, or a wired connection, for example to communicatively connect the devices 102*a-b*, 104*a-b*, and 106*a-b*.

Any portion of system 100, e.g., devices 102, 104, and 106 and server 114, may include a computing system and/or device that includes a processor 105 and a memory 107. Computing systems and/or devices generally include computer-executable instructions, where the instructions may be executable by one or more devices such as those listed below. Computer-executable instructions may be compiled or interpreted from computer programs created using a variety of programming languages and/or technologies, including, without limitation, and either alone or in combination, Java™, C, C++, Visual Basic, Java Script, Perl, SQL, PL/SQL, Shell Scripts, etc. The system 100, e.g., devices 102, 104, and 106 and server 114 may take many different forms and include multiple and/or alternate components and facilities, as illustrated in the Figures further described below. While exemplary systems, devices, modules, and sub-modules are shown in the Figures, the exemplary components illustrated in the Figures are not intended to be limiting. Indeed, additional or alternative components and/or implementations may be used, and thus the above communication operation examples should not be construed as limiting.

In general, computing systems and/or devices (e.g., devices 102, 104, and 106 and server 114) may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., the BlackBerry OS distributed by Research In Motion of Waterloo, Canada, and the Android operating system developed by the Open Handset Alliance. Examples of computing systems and/or devices such as devices 102, 104, and 106 and server 114 may include, without limitation, mobile devices, cellular phones, smart-phones, super-phones, tablet computers, next generation portable devices, mobile printers, handheld computers, notebooks, laptops, secure voice communication equipment, networking hardware, computer workstations, or any other computing system and/or device.

Further, processors such as processor 105 receive instructions from memories such as memory 107 or database 115 and execute the instructions, thereby performing one or more processes, including one or more of the processes described herein. Such instructions and other occupant information may be stored and transmitted using a variety of computer-readable mediums (e.g., memory 107 or database 115). Processors such as processor 105 may include any computer hardware or combination of computer hardware that is configured to accomplish the purpose of the devices, systems, and processes described herein. For example, the processor 105 may be any one of, but not limited to single, dual, triple, or quad core processors (on one single chip), graphics processing units, visual processing units, and virtual processors.

A memories such as memory 107 or database 115 may include, in general, any computer-readable medium (also referred to as a processor-readable medium) that may include any non-transitory (e.g., tangible) medium that participates in providing occupant information or instructions that may be read by a computer (e.g., by the processors 105 of the devices 102, 104, and 106 and server 114). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including radio waves, metal wire, fiber optics, and the like, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

The devices 102, 104, and 106 and server 114 may include processor 105 that is configured to perform operations with respect to the occupant information, for example update and store occupant information as part of memory 107 or database 115. The devices 102, 104, and 106 and server 114 may further utilize the processor 105 to transfer and display occupant information, as described herein.

Further, databases, data repositories or other occupant information stores (e.g., memory 107 and database 115) described herein may generally include various kinds of mechanisms for storing, providing, accessing, and retrieving various kinds of occupant information, including a hierarchical database, a set of files in a file system, an application database in a proprietary format, a relational database management system (RDBMS), etc. Each such occupant information store may generally be included within (e.g., memory 107) or external (e.g., database 115) to a computing system and/or device (e.g., devices 102, 104, and 106 and server 114) employing a computer operating system such as one of those mentioned above, and/or accessed via a network (e.g., system 100 or subscriber network 117) or connection in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

Figure 2:
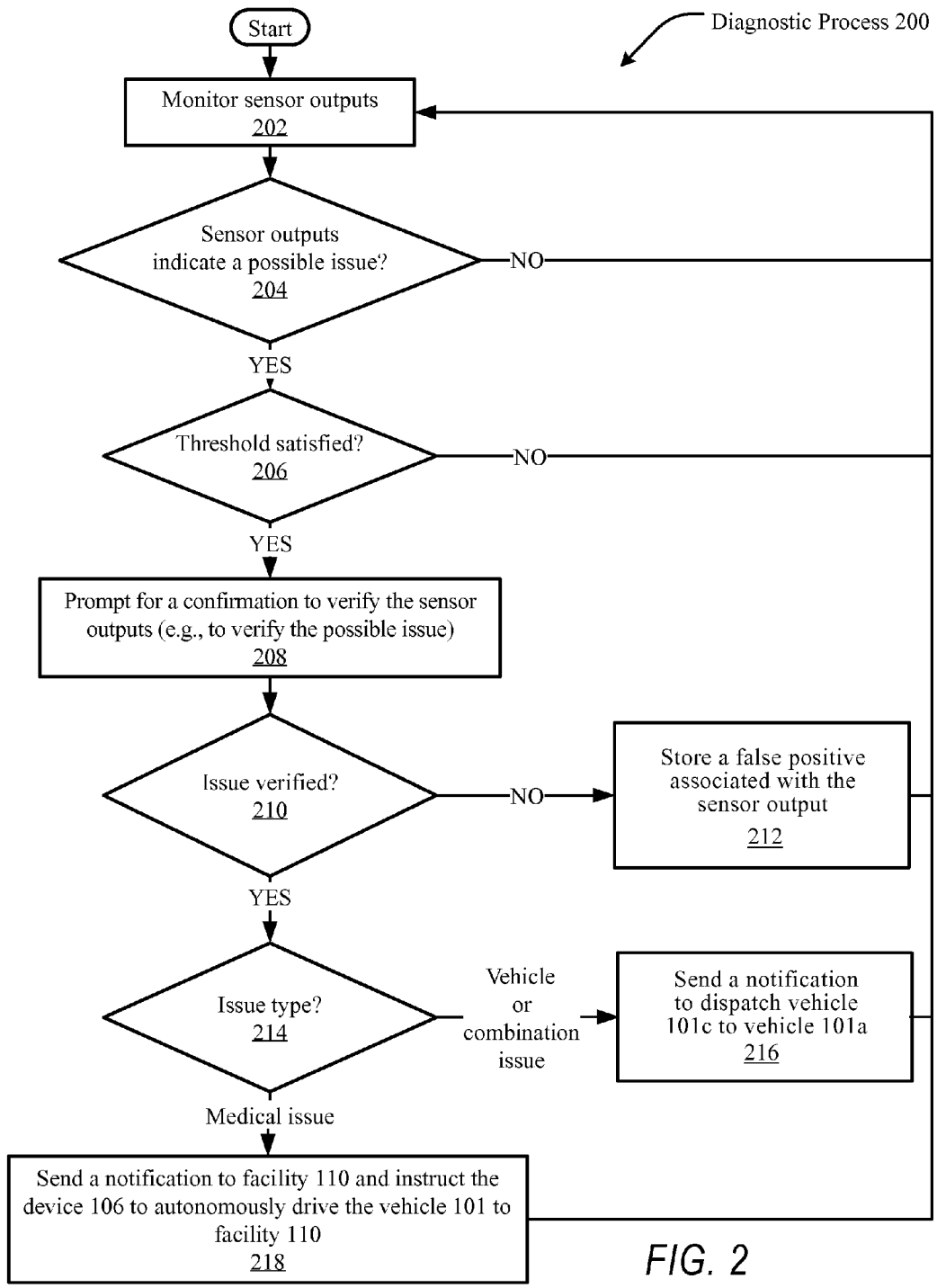
FIG. 2 illustrates an exemplary diagnostic process.

FIG. 2 illustrates an exemplary diagnostic process 200. Process 200 may take many different forms and include multiple and/or alternate components and facilities. While an exemplary process 200 is shown in FIG. 2, the exemplary components illustrated in FIG. 2 are not intended to be limiting. Indeed, additional or alternative components and/or implementations may be used.

At block 202, the device 102 may monitor one or more sensor outputs from one or a plurality of sensors 112, e.g., vehicle sensors, body sensors, or a combination thereof. Moreover, as noted above, inputs from a plurality of different sensors 112 may be agglomerated. For example, the one or more sensor outputs may be associated with a possible issue, e.g., a medical issue associated with occupant 121 from a body sensor output from a body sensor, a vehicle issue associated with the vehicle 101 from a vehicle sensor output from a vehicle sensor, or a combination issue including both medical and vehicle issues from body and vehicle sensors.

At decision point 204, the device 102, using the processor 105, may determine if the sensor outputs from the one or a plurality of sensors 112 indicate a possible issue. If the sensor outputs are not associated with a possible issue, the device 102 may continue to monitor sensor outputs. If the sensor outputs are associated with a possible issue, the device 102 may determine if the sensor outputs satisfy a threshold.

At decision point 206, the device 102, using the processor 105, may determine if the sensor outputs satisfy the threshold. The threshold may include a threshold number, a threshold sequence, a lower threshold, an upper threshold, or a threshold range, as discussed above. If multiple sensors 112 are being used, the combined output of the sensors 112 may result in the determination of an issue even if the output from any one sensor by itself may not confirm such an issue. The device 102 may generate the determination in response to two or more sensor outputs confirming the issue. For example, a first sensor (e.g., a moisture sensor) may generate a first sensor output in response to a spilled drink, which may not meet the threshold. However, if a first sensor (e.g., a moisture sensor) and a second sensor (e.g., a chemical sensor) generate respective first and second sensor outputs in response to a body fluid, the threshold may be satisfied. As a further example, the threshold may be satisfied by a vehicle sensor output and a body sensor output occurring within a predefined time period, e.g., indicating a vehicle crash and resulting injuries, as discussed above. Thus, a decision tree may be appropriate in the case of reviewing data from a plurality of sensors 112 that is more sophisticated than solely relying on the threshold range of a single sensor 112. As a result, the exemplary step recognizes that the threshold determination may involve the consideration of multiple sensor outputs, whether from a single sensor over time or a plurality of sensors.

If the threshold is not satisfied, the device 102 may continue to monitor sensor outputs. If the threshold is satisfied, the device 102 may prompt for a confirmation from occupant 121 to verify the sensor outputs (e.g., to verify the possible issue).

At block 208, the device 102 may prompt the occupant 121 for a confirmation to verify the sensor outputs (e.g., to verify the possible issue) using the user interface 111.

At decision point 210, the device 102 may determine if the confirmation verifies the sensor output, e.g., thereby verifying the issue. For example, the occupant 121 may verbally indicate that there is no issue, which is inconsistent with the sensor output thereby failing to verify the issue. Alternatively, the occupant 121 may verbally indicate that there is an issue (e.g., a medical issue, a vehicle issue, or a combination issue) or may be silent (e.g., indicating incapacitation due to a medical issue or a combination issue), thereby confirming the sensor output. If the confirmation and sensor output are inconsistent, the device 102 may store a false positive associated with the sensor output and continue to monitor the sensor outputs. If the confirmation and sensor output are consistent thereby verifying the issue, the device 102 may determine if the vehicle is inoperable.

At block 212, if the confirmation indicates that the medical issue is not present, device 102 may instruct device 106 to allow the vehicle 101 to continue in the current driving mode and store a false positive associated with the issue as part of the memory 107 or database 115. Alternatively, the processor 105 may determine that a medical condition exists based on a lack of confirmation at block 212.

At decision point 214, the device 102 may determine the issue type including, for example, a medical issue, a vehicle issue, or a combination issue. For example, the type of issue may be used to determine if medical treatment based on a medical issue, if the vehicle 101 is inoperable thereby requiring roadside assistance based on a vehicle issue, or a combination issue requiring both. For example, the device 102 may check the sensor outputs to determine if vehicle and medical issues are present. If the sensor outputs include a vehicle issue, then the device 102 may determine that the vehicle 101*a* is not inoperable and send a notification to dispatch vehicle 101*c* (e.g., roadside assistance) to vehicle 101*a*. If the sensor outputs include a combination issue, then the device 102 may determine that the vehicle 101*a* is not inoperable and send a notification to dispatch vehicle 101*c* (e.g., roadside assistance and an ambulance) to vehicle 101*a*. If the sensor outputs include a medical issue but not a vehicle issue, then the device 102 may determine that the vehicle 101*a* is inoperable, send a notification to the facility 110, and drive the vehicle 101 to facility 110 in the autonomous driving mode.

At block 216, the device 102 may send a notification to dispatch vehicle 101*c* (e.g., an emergency vehicle) to vehicle 101*a* and continue to monitor the sensor outputs.

At block 218, if the confirmation indicates that the medical issue is present, instruct the device 106 to operate the vehicle 101 using the semi-autonomous or autonomous driving mode, e.g., to drive the vehicle 101 to facility 110, and send a notification including the confirmed medical issue to the facility 110 using the transceiver 109. For example, the notification may allow the facility 110 to prepare for the arrival of the occupant 121, as discussed above. After block 212, the device 102 may continue to monitor the sensor outputs.

Figure 3:
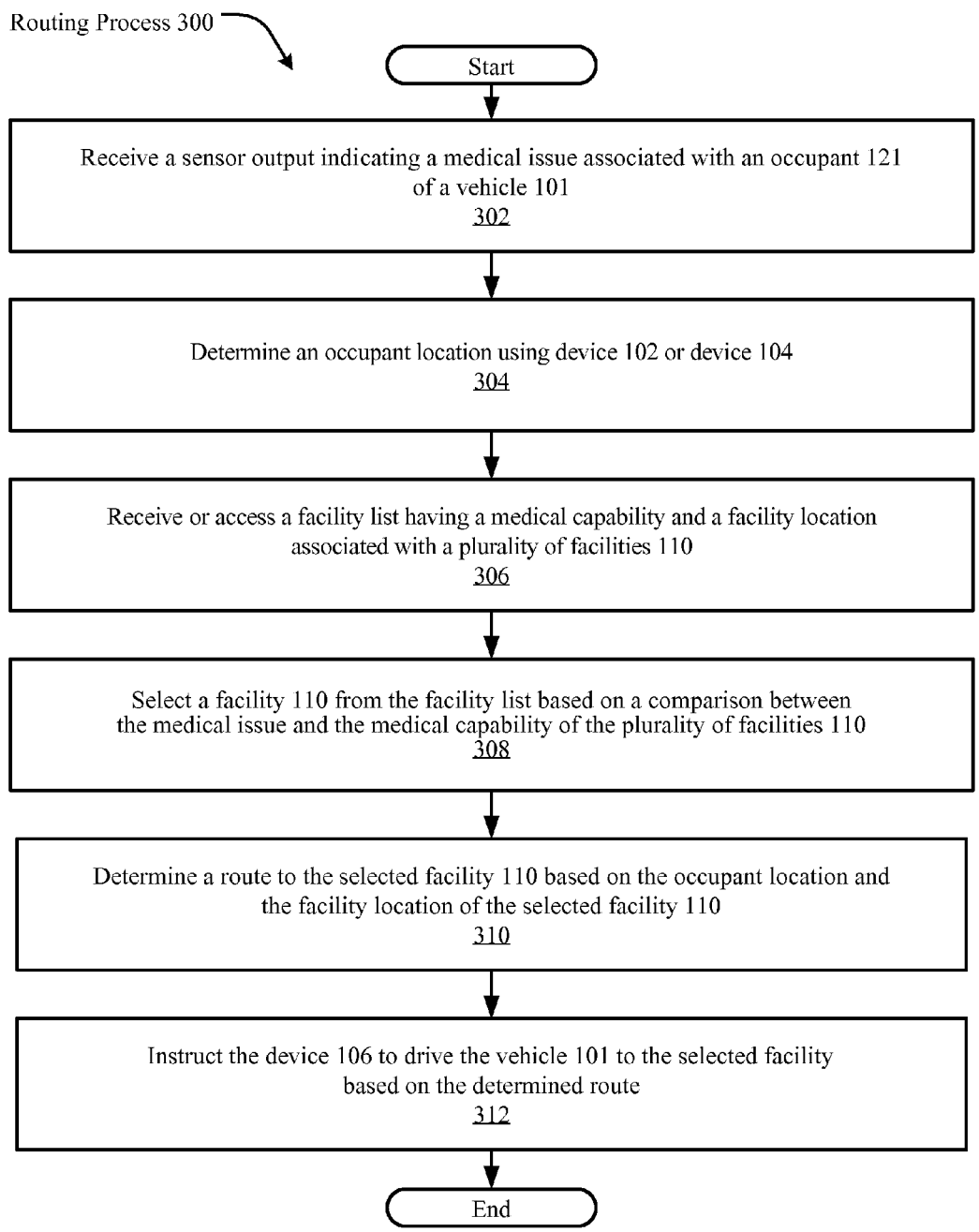
FIG. 3 illustrates an exemplary routing process.

FIG. 3 illustrates an exemplary routing process 300. Process 300 may take many different forms and include multiple and/or alternate components and facilities. While an exemplary process 300 is shown in FIG. 3, the exemplary components illustrated in FIG. 3 are not intended to be limiting. Indeed, additional or alternative components and/or implementations may be used.

At block 302, the device 102 or 104, using the transceiver 109, or server 114 may receive a sensor output indicating a medical issue associated with an occupant 121 of a vehicle from the sensor 112.

At block 304, the device 102 or 104, e.g., using the GPS, may determine an occupant location.

At block 306, the device 102 or 104, using the transceiver 109, or the server 114 may access or receive a facility list, as part of the memory 107 or database 115, having medical capabilities and facility locations associated with a plurality of facilities 110.

At block 308, the processor 105 of device 102 or 104 or server 114 may select a facility 110 from the facility list based on a comparison between the medical issue and the medical capabilities of the plurality of facilities 110.

At block 310, if the confirmation indicates a medical issue, the device 102 or 104, using the transceiver 109, may instruct the device 106 to operate the vehicle 101 using an autonomous driving mode, or partial or semi-autonomous mode, and, in addition, the device 102 or 104 may send, using the transceiver 109, a notification including the confirmed medical issue to another device 102 or server 114 using the transceiver 109.

At block 312, if the confirmation or lack of confirmation indicates no medical issue, the device 102 or 104, using the transceiver 109, may instruct the device 106 allow the vehicle 101 to continue in a current driving mode and, in addition, the device 102 or 104 may store, as part of the memory 107 or database 115, a false positive associated with the sensor 112. After block 312, the process 300 ends.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Figure 4:
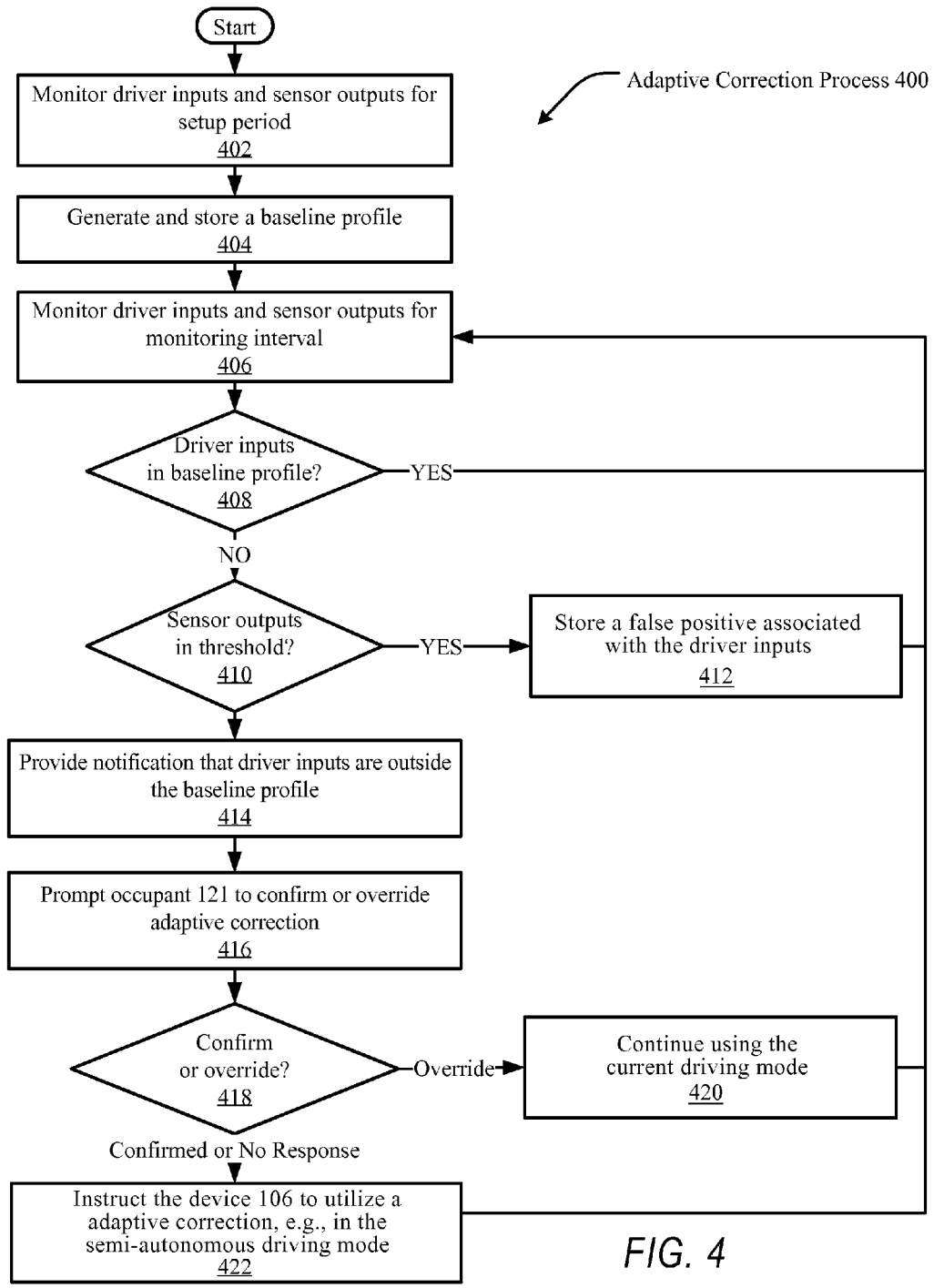
FIG. 4 illustrates an exemplary adaptive correction process.

FIG. 4 illustrates an exemplary adaptive correction process 400. Process 400 may take many different forms and include multiple and/or alternate components and facilities. While an exemplary process 400 is shown in FIG. 4, the exemplary components illustrated in FIG. 4 are not intended to be limiting. Indeed, additional or alternative components and/or implementations may be used.

At block 402, the sensor 112 may monitor driver inputs and sensor outputs for a setup period, as discussed above.

At block 404, the device 102 or 104, e.g., using the processor 105, may generate and store a baseline profile, e.g., as part of memory 107.

At block 406, the device 102 or 104, e.g., using the processor 105, may monitor the driver inputs and sensor outputs for a monitoring interval.

At decision point 408, the device 102 or 104, e.g., using the processor 105, determine if the driver inputs are in the baseline profile. If the driver inputs are in the baseline profile, the processor may continue to monitor the driver inputs and sensor outputs. If the driver inputs are not in the baseline profile, the processor 105 may determine if the sensor outputs are in a threshold, as discussed above.

At decision point 410, the device 102 or 104, e.g., using the processor 105, may determine if the sensor outputs are in the threshold. If the sensor outputs are in the threshold, the processor 105 may store a false positive, e.g., as part of memory 107. If the sensor outputs are not in the threshold, the processor 105 may provide a notification.

At block 412, the device 102 or 104, e.g., using the processor 105, may store a false positive, e.g., as part of memory 107.

At block 414, the device 102 or 104, e.g., using the processor 105, may provide a notification, e.g., to another device 102 or 104 or server 114, confirm or override adaptive correction, as discussed above.

At block 416, the device 102 or 104, e.g., using the processor 105, may provide prompt occupant 121 to confirm or override adaptive correction, as discussed above.

At decision point 418, the device 102 or 104, e.g., using the user interface 111, may receive a confirmation to accept or override adaptive correction. If the confirmation indicates that adaptive correction is accepted or no response is received, the device 102 or 104 may instruct device 106 to utilize adaptive correction. If the confirmation indicates that adaptive correction is overridden, the device 106 may continue using the current driving mode.

At block 420, the device 106, e.g., using the processor 105, may continue using the current driving mode.

At block 422, the device 102 or 104, e.g., using the transceiver 109, may instruct the device 106 to utilize adaptive correction, e.g., in the semi-autonomous driving mode.

After block 422, the process 400 restarts at block 406.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A system comprising:
   a user interface;
   a processor and a memory having a program communicatively connected to the processor, the processor being configured to:
   receive a body sensor output associated with an occupant of a vehicle;
   receive a vehicle sensor output associated with the vehicle;
   compare, using the processor, at least one of the body and vehicle sensor outputs with a threshold;
   prompt, using the user interface, for a confirmation associated with at least one of the body and vehicle sensor outputs;
   determine, using the processor, an issue type based on at least one of the body and vehicle sensor outputs;
   send a notification including the issue type;
   receive a facility list having a medical capability and a facility location for a plurality of facilities;

select, using the processor, one of the plurality of facilities from the facility list based in part on a comparison between the medical issue and the medical capability of at least a portion of the plurality of facilities; and determine, using the processor, a route to the selected one of the plurality of facility.

2. The system of claim 1, wherein the issue type includes a medical issue associated with the occupant.

3. The system of claim 2, wherein the issue type further includes a vehicle issue associated with the vehicle.

4. The system of claim 1, the processor further being configured to instruct a vehicle computer of the vehicle to change from a current driving mode to an autonomous driving mode.

5. The system of claim 1, the processor further being configured to instruct a vehicle computer of the vehicle to drive the vehicle to the selected facility based on the determined route.

6. The system of claim 1, wherein the notification includes the issue type and is sent to at least one of a facility and an emergency vehicle.

7. A non-transitory computer-readable medium tangibly embodying computer-executable instructions of a program being executable by a processor of a computing device to provide operations comprising:

receive a body sensor output associated with an occupant of a vehicle;

receive a vehicle sensor output associated with the vehicle;

compare, using the processor, the body and vehicle sensor outputs with a threshold;

prompt, using the user interface, for a confirmation associated with the body and vehicle sensor outputs;

determine, using the processor, an issue type based on the body and vehicle sensor outputs;

send a notification including the issue type;

receive a facility list having a medical capability and a facility location for a plurality of facilities;

select one of the plurality of facilities from the facility list based in part on a comparison between the medical issue and the medical capability of at least a portion of the plurality of facilities; and determine a route to the selected one of the plurality of facilities.

8. The medium of claim 7, wherein the issue type includes a medical issue associated with the occupant.

9. The medium of claim 8, wherein the issue type further includes a vehicle issue associated with the vehicle.

10. The medium of claim 7, the operations further comprising instruct a vehicle computer of the vehicle to change from a current driving mode to an autonomous driving mode.

11. The medium of claim 7, the operations further comprising instruct a vehicle computer of the vehicle to drive the vehicle to the selected facility based on the determined route.

12. The medium of claim 7, wherein the notification includes the issue type and is sent to at least one of a facility and an emergency vehicle.

13. A method comprising:

receiving a body sensor output associated with an occupant of a vehicle;

receiving a vehicle sensor output associated with the vehicle;

comparing, by way of a processor, at least one of the vehicle and body sensor outputs with a threshold;

prompting, by way of a user interface, for a confirmation associated with the at least one of the body and vehicle sensor outputs;

determining, by way of the processor, an issue type based on at least one of the body and vehicle sensor outputs;

sending a notification including the issue type;

receiving a facility list having a medical capability and a facility location for a plurality of facilities;

selecting, using a processor, one of the plurality of facilities from the facility list based in part on a comparison between the medical issue and the medical capability of at least a portion of the plurality of facilities; and determining, without human intervention, a route to the selected one of the plurality of facilities.

14. The method of claim 13, wherein the issue type includes a medical issue associated with the occupant.

15. The method of claim 14, wherein the issue type further includes a vehicle issue associated with the vehicle.

16. The method of claim 13, the method further comprising instructing the vehicle to change from a current driving mode to an autonomous driving mode.

17. The method of claim 13, the method further comprising instructing a vehicle computer of the vehicle to drive the vehicle to the selected facility based on the determined route.

* * * * *